US012599502B2

(12) United States Patent
Bor

(10) Patent No.: US 12,599,502 B2
(45) Date of Patent: Apr. 14, 2026

(54) REDUCING RETINAL RADIATION EXPOSURE DURING LASER SURGERY

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 657 days.

(21) Appl. No.: 18/049,550

(22) Filed: Oct. 25, 2022

(65) Prior Publication Data

US 2023/0157880 A1 May 25, 2023

Related U.S. Application Data

(60) Provisional application No. 63/281,437, filed on Nov. 19, 2021.

(51) Int. Cl.
*A61F 9/008* (2006.01)
*A61B 18/00* (2006.01)
(Continued)

(52) U.S. Cl.
CPC .... *A61F 9/008* (2013.01); *A61B 2018/00904* (2013.01); *A61B 2018/20353* (2017.05);
(Continued)

(58) Field of Classification Search
CPC ...................................................... A61F 9/008
See application file for complete search history.

(56) References Cited

U.S. PATENT DOCUMENTS 3,780,979 A 12/1973 De
4,357,088 A 11/1982 Pomerantzeff
(Continued)

FOREIGN PATENT DOCUMENTS

AU 2018274939 B2 6/2020
CN 210009227 U 2/2020
(Continued)

OTHER PUBLICATIONS

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.
(Continued)

*Primary Examiner* — Lynsey C Eiseman
(74) *Attorney, Agent, or Firm* — Patterson + Sheridan, LLP

(57) ABSTRACT

In certain embodiments, an ophthalmic laser surgical system for treating a floater in a vitreous of an eye includes a floater detection system, a laser device, and a computer. The floater detection system determines the location of the floater in the vitreous of the eye. The laser device directs a laser beam along a laser beam path towards the floater. The computer accesses a three-dimensional scan pattern for the laser beam that yields a three-dimensional pulse pattern of laser pulses. The three-dimensional pulse pattern has a bubble shield pulse pattern at the posterior side of the three-dimensional pulse pattern. The bubble shield pulse pattern forms a bubble shield that reduces laser radiation exposure at a retina of the eye. The computer instructs the laser device to direct the laser beam towards the floater according to the three-dimensional scan pattern.

9 Claims, 4 Drawing Sheets

(51) Int. Cl.
        *A61B 18/20*         (2006.01)
        *A61B 90/00*         (2016.01)
(52) U.S. Cl.
        CPC .................. *A61B 2090/049* (2016.02); *A61F*
                                    *2009/00874* (2013.01)

(56)                    References Cited

U.S. PATENT DOCUMENTS

| | | | |
|---|---|---|---|
| 5,312,396 | A | 5/1994 | Feld |
| 5,909,270 | A | 6/1999 | Moser |
| 6,142,630 | A | 11/2000 | Koester |
| 6,322,556 | B1 | 11/2001 | Gwon |
| 6,789,900 | B2 | 9/2004 | Van De Velde |
| 7,374,287 | B2 | 5/2008 | Van De Velde |
| 7,510,282 | B2 | 3/2009 | Ueno |
| 7,520,613 | B2 | 4/2009 | Saito et al. |
| 7,703,922 | B2 | 4/2010 | Van De Velde |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0103010 | A1* | 4/2013 | Grant .................. A61F 9/00825 |
| | | | 606/4 |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0028354 | A1* | 2/2018 | Heeren .................. G16H 30/40 |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |

| | | | |
|---|---|---|---|
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |

(56) References Cited

FOREIGN PATENT DOCUMENTS

| | | | |
|----|----------------|----|--------|
| WO | 2021023799 A1 | | 2/2021 |
| WO | 2021049243 A1 | | 3/2021 |
| WO | 2021066047 A1 | | 4/2021 |
| WO | 2021092211 A1 | | 5/2021 |
| WO | 2021183637 A1 | | 9/2021 |
| WO | 2022149028 A1 | | 7/2022 |
| WO | 2023089416 A1 | | 5/2023 |
| WO | 2023089459 A1 | | 5/2023 |
| WO | 2023097391 A1 | | 6/2023 |

OTHER PUBLICATIONS

Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light-Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/floater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

Adrian G.H. Podoleanu et al., Combined optical coherence tomograph and scanning laser ophthalmoscope minije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010; 149(4):641-650.

Nidek, Scanning Laser Ophthalmoscope Mirante SLO/OCT Mirante SLO, https://www.nidek-intl.com/product/ophthaloptom/diagnostic/dia_retina/mirante.htm.

Peter G. J. Barten, "Contrast Sensitivity of the Human Eye and its Effects on Image Quality," Chapter 3, pp. 27-40, Model for the spatial contrast sensitivity of the eye, (1999).

Pointer, J. S., & Hess, R. F. "The contrast sensitivity gradient across the human visual field: With emphasis on the low spatial frequency range,", R. F. Vision Research, 29(9), 1133-1151 (1989).

Sebag J et al., Vitreous and Vitreoretinal Interface, Ch. 21, 2015.

Sebag J., Vitreous and Vision Degrading Myodesopsia. Progress in Retinal and Eye Research Nov. 2020;79.

T Ivanova et al, Vitrectomy for primaryvsymptomatic vitreous opacities: an evidence-based review, Eye (Lond) May 2016;30(5):645-55.

Teri T Kleinberg et al., Vitreous substitutes: a comprehensive review, Survey of Ophthalmology, 56 (4), 2011.

Damodaran et al., "Digital micromirror device based ophthalmoscope with concentric circle scanning", 2017, pp. 2766-2780, vol. 8, No. 5, Biomedical Optics Express.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering GMBH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, PLOS One.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3x3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim At Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/ . . . s?pr_prod_strat=collection_fallback&pr_rec_pid=4513049018402&pr_ref_pid=4513048952866&pr_seq=uniform.

Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;amp;_sid=b50c0674f&amp;amp;_ss=r.

(56) References Cited

OTHER PUBLICATIONS

Wang et al., "In vivo full range complex Fourier domain optical coherence tomography", Jan. 30, 2007, 054103, vol. 90, Applied Physics Letters.

Wojtkowski et al., "Full range complex spectral optical coherence tomography technique in eye imaging", 2002, pp. 1415-1417, vol. 27, No. 16, Optics Letters.

Yasuno et al., "Simultaneous B—M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

* cited by examiner

IMAGE
60

MOVING FLOATER
SHADOWS
68

RETINA
62

68a

68b

64
FOVEA

66
PARAFOVEA

68c

REDUCING RETINAL RADIATION EXPOSURE DURING LASER SURGERY

TECHNICAL FIELD

The present disclosure relates generally to laser vitreolysis systems, and more particularly to reducing retinal radiation exposure during laser surgery.

BACKGROUND

In laser vitreolysis, a laser beam is directed into the vitreous to treat vitreous eye floaters. Eye floaters are microscopic collagen fibers that tend to clump and cast shadows on the retina, which disturb the vision of the patient. The laser beam disintegrates the floaters to improve vision.

BRIEF SUMMARY

In certain embodiments, an ophthalmic laser surgical system for treating a floater in a vitreous of an eye includes a floater detection system, a laser device, and a computer. The floater detection system determines the location of the floater in the vitreous of the eye. The laser device directs a laser beam along a laser beam path towards the floater. The computer accesses a three-dimensional scan pattern for the laser beam that yields a three-dimensional pulse pattern of laser pulses. The three-dimensional pulse pattern has a bubble shield pulse pattern at the posterior side of the three-dimensional pulse pattern. The bubble shield pulse pattern forms a bubble shield that reduces laser radiation exposure at a retina of the eye. The computer instructs the laser device to direct the laser beam towards the floater according to the three-dimensional scan pattern.

Embodiments may include none, one, some, or all of the following features:

The computer instructs the laser device to scan a posterior portion of the three-dimensional scan pattern prior to scanning an anterior region of the three-dimensional scan pattern.

The ophthalmic laser system includes an xy-scanner that: receives a detection beam from the floater detection system and directs the detection beam along the detection beam path towards an xy-location of the floater; and receives the laser beam from the laser device and directs the laser beam along the detection beam path towards the xy-location of the floater.

In certain embodiments, a method for treating a floater in a vitreous of an eye comprises determining, by a floater detection system, the location of the floater in the vitreous of the eye. A three-dimensional scan pattern for a laser beam that yields a three-dimensional pulse pattern of laser pulses is accessed by a computer. The three-dimensional pulse pattern comprises a bubble shield pulse pattern at a posterior side of the pattern. The bubble shield pulse pattern forms a bubble shield that reduces laser radiation exposure at the retina of the eye. A laser device is instructed by the computer to direct the laser beam towards the floater according to the three-dimensional scan pattern. The laser beam is directed by the laser device along a laser beam path towards the floater.

Embodiments may include none, one, some, or all of the following features:

Instructing the laser device to direct the laser beam towards the floater according to the three-dimensional scan pattern comprises instructing the laser device to scan the posterior portion of the three-dimensional scan pattern prior to scanning the anterior region of the three-dimensional scan pattern.

A detection beam from the floater detection system is received by an xy-scanner and directed along the detection beam path towards an xy-location of the floater. The laser beam from the laser device is received by the xy-scanner and directed along the detection beam path towards the xy-location of the floater.

In certain embodiments, an ophthalmic laser surgical system for treating a floater in a vitreous of an eye includes a floater detection system, a laser device, and a computer. The floater detection system determines a location of the floater in the eye. The laser device directs a laser beam along a laser beam path towards the floater. The computer: calculates a radiant exposure at a component of the eye according to a floater-to-component distance between a z-location of the floater and the component; calculates a safety factor from the radiant exposure, the safety factor describing a mathematical relationship between the radiant exposure and a maximum exposure; determines if directing the laser beam along the laser beam path towards the floater is allowable according to a predetermined boundary of the safety factor; and instructs the laser device to direct the laser beam along the laser beam path towards the floater if that is allowable.

Embodiments may include none, one, some, or all of the following features:

The safety factor is equal to the ratio of the maximum exposure and the radiant exposure.

The radiant exposure describes radiant exposure at a retina of the eye, and the maximum radiant exposure describes a maximum radiant exposure for a single pulse at the retina.

The radiant exposure describes radiant exposure at a retina of the eye, and the maximum radiant exposure describes a maximum average power at the retina.

The radiant exposure describes radiant exposure at a lens of the eye, and the maximum exposure describes a maximum radiant exposure at the lens.

The computer calculates the radiant exposure at the component of the eye according to the z-location of the floater by: determining a laser spot size of the laser beam on the component; and calculating the radiant exposure according to the laser spot size of the laser beam and the floater-to-component distance.

The computer calculates a closest floater-to-component distance at which the eye can be treated, given a laser pulse energy of the laser beam.

The computer calculates a maximum laser pulse energy at which the eye can be treated, given the floater-to-component distance.

If directing the laser beam along the laser beam path towards the floater is not allowable, the computer prevents the laser device from directing the laser beam towards the floater.

In certain embodiments, a method for treating a floater in an eye comprises determining, by a floater detection system, the location of the floater in the eye. The radiant exposure at a component of the eye is calculated by a computer according to the floater-to-component distance between the z-location of the floater and the component. A safety factor is calculated from the radiant exposure by a computer. The safety factor describes a mathematical relationship between the radiant exposure and a maximum exposure. Whether directing a laser beam along the laser beam path towards the floater is allowable according to a predetermined boundary of the safety factor is determined by the computer. A laser device is instructed by the computer to direct the laser beam along a laser beam path towards the floater if that is allowable. The laser beam is directed by the laser device along the laser beam path towards the floater.

Embodiments may include none, one, some, or all of the following features:

The safety factor is equal to the ratio of the maximum exposure and the radiant exposure.

The radiant exposure describes radiant exposure at a retina of the eye, and the maximum radiant exposure describes a maximum radiant exposure for a single pulse at the retina.

The radiant exposure describes radiant exposure at a retina of the eye, and the maximum radiant exposure describes a maximum average power at the retina.

The radiant exposure describes radiant exposure at a lens of the eye, and the maximum exposure describes a maximum radiant exposure at the lens.

Calculating the radiant exposure at the component of the eye according to the z-location of the floater comprises: determining the laser spot size of the laser beam on the component; and calculating the radiant exposure according to the laser spot size of the laser beam and the floater-to-component distance.

A closest floater-to-component distance at which the eye can be treated, given a laser pulse energy of the laser beam, is calculated by the computer.

A maximum laser pulse energy at which the eye can be treated, given the floater-to-component distance, is calculated by the computer.

If directing the laser beam along the laser beam path towards the floater is not allowable, the laser device is prevented from directing the laser beam towards the floater by the computer.

DESCRIPTION OF EXAMPLE EMBODIMENTS

Figure 1:
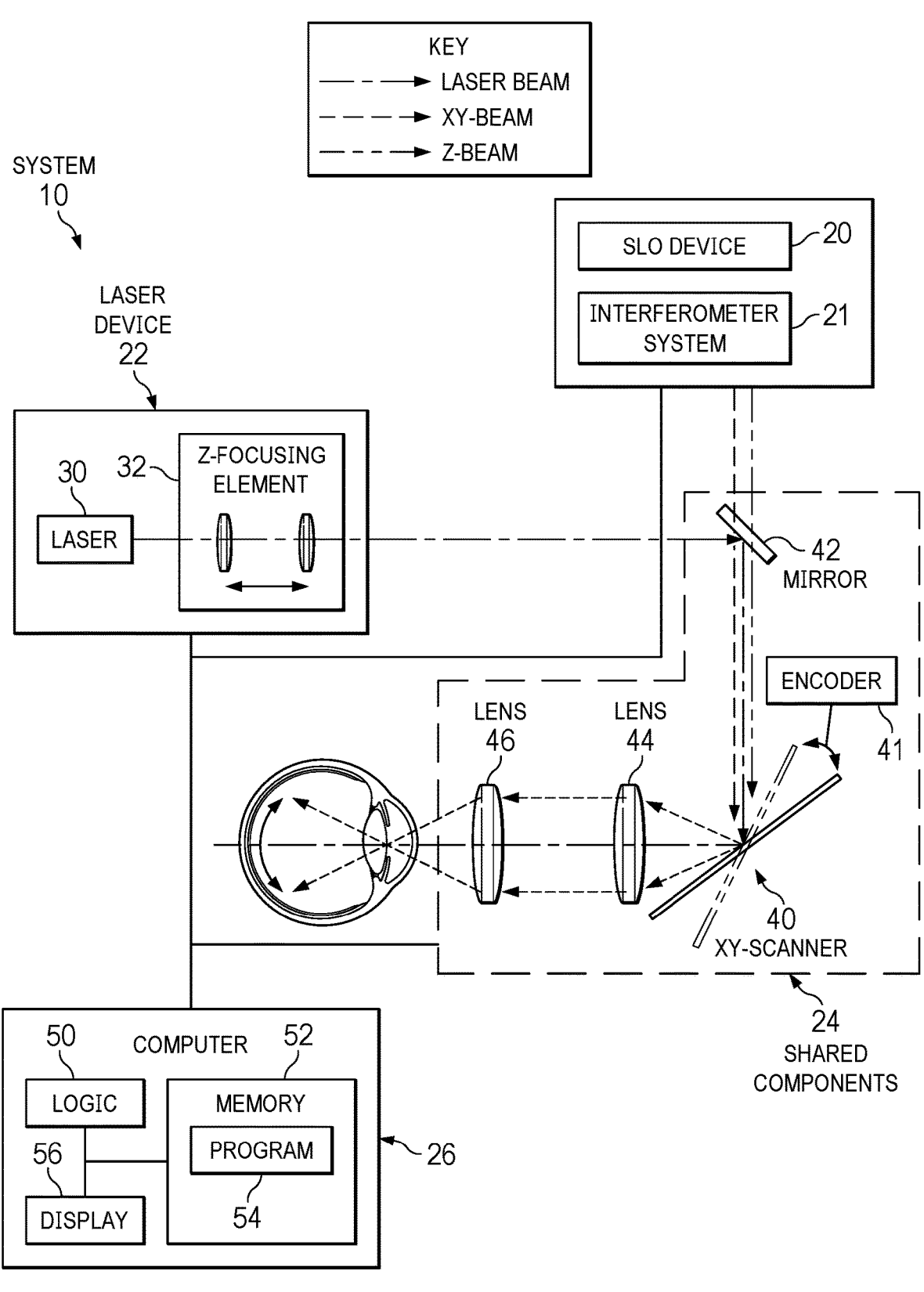
FIG. 1 illustrates an example of an ophthalmic laser surgical system that may be used to treat a floater in an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Laser vitreolysis is performed to remove eye floaters. However, care must be taken to not overexpose the retina to laser radiation. Accordingly, an ophthalmic laser surgical system reduces exposure of the retina by creating a gas bubble shield that protects the retina from overexposure. In addition, the system uses multiple laser pulses to fragment a floater more efficiently and to reduce the likelihood of unpredictable floater movement. Furthermore, the system calculates safety factors that can be used to evaluate whether a procedure will cause too much retinal exposure.

FIG. 1 illustrates an example of an ophthalmic laser surgical system 10 that may be used to treat a floater in an eye, according to certain embodiments. In the embodiments, a floater detection system determines the location of a floater in an eye. A computer instructs a laser device to direct a three-dimensional (3D) pattern of laser pulses towards the floater. The pattern includes a bubble shield that reduces radiation exposure at the retina of the eye. The laser device directs a laser beam towards the floater according to the pattern.

As an overview, system 10 includes a floater detection system 19, a laser device 22, one or more shared components 24, and a computer 26, coupled as shown. Floater detection system 19 includes a scanning laser ophthalmoscope (SLO) device 20 and an interferometer device 21. Laser device 22 includes an ultrashort pulse laser 30 and a z-focusing component 32, coupled as shown. Shared components 24 include an xy-scanner 40, an xy-encoder 41, and optical elements (such as a mirror 42 and lenses 44 and 46), coupled as shown. Computer 26 includes logic 50, a memory 52 (which stores a computer program 54), and a display 56, coupled as shown.

As an overview of operation of system 10, xy-scanner 40 receives an SLO beam from SLO device 20 and directs the SLO beam along an SLO beam path towards the eye. SLO device 20 generates an SLO image of the floater shadow cast by a floater onto the retina. SLO device 20 also provides the xy-location of the floater shadow, where the xy-location is related to xy-scanner 40. Interferometer device 21 provides the z-distance of the floater from the retina (which may be referred to as the z-location). Z-focusing component 32 of laser device 22 receives the z-location of the floater from interferometer device 21 and focuses the focal point of the laser beam onto the z-location of the floater. Computer 26 instructs laser device 22 to direct a three-dimensional (3D) pattern of laser pulses towards the floater. The pattern includes a bubble shield that reduces radiation exposure at the retina of the eye. Xy-scanner 40 receives the laser beam from the laser device and directs the laser beam along the SLO beam path towards the xy-location of the floater shadow according to the 3D pattern.

Turning to the parts of the system, floater detection system 19 includes one or more detection devices that detect, locate, and/or image a floater and/or a floater shadow cast by the floater on the retina. To detect, locate, and/or image a floater and/or a floater shadow, a detection device directs a detection beam along a detection beam path towards the interior of the eye. The interior reflects the detection beam, and the device detects the reflected light and detects, locates, and/or images a floater and/or a floater shadow.

In certain embodiments, floater detection system 19 includes SLO device 20 and interferometer device 21. SLO device 20 utilizes confocal laser scanning to generate images of the interior of the eye. In certain embodiments, SLO device 20 generates an image of the floater shadow that a floater casts on the retina and provides the xy-location of the floater shadow in encoder units. Interferometer device 21 provides the z-location of the floater relative to the retina. Interferometer device 21 has any suitable interferometer, e.g., a Fourier domain type (such as a swept source or a spectral domain type) that utilizes a fast Fourier transform (FFT). Examples of interferometer device 21 include an optical coherence tomography (OCT) device (such as a swept-source OCT device) and a swept source A-scan interferometer (SSASI) device (where a SASSI device performs only A-scans). Swept Source OCT and SSASI devices have a measuring range up to about 30 millimeters (mm) that can measure the depth (i.e., z-location relative to the retina) within the full length of the eye from the cornea to the retina.

Turning to laser device 22, laser 30 may generate ultrashort laser pulses. Unlike YAG lasers currently used for laser vitreolysis, an ultrashort pulse laser may be used without harming the retina. On the one hand, YAG laser emits longer pulses with a higher pulse energy (e.g., 5 millijoules (mJ)). However, the higher pulse energy yields retinal exposure that exceeds the ANSI Retinal Maximum Permissible Exposure (MPE) at floater-to-retina distances where clinically significant floaters are typically located, around 3 mm or closer to the retina. For example, given pulse energy PE=5 mJ, laser beam numerical aperture NA=0.1, and floater-to-retina distance D=3 millimeters (mm)=0.3 centimeters (cm), the energy density ED on the retina is approximately $ED=PE/(D*2NA)^2=5$ $mJ/(0.3$ $cm*0.2)^2=1.39$ $J/cm^2$. The ANSI Retinal Maximum Permissible Exposure MPE for a nanosecond pulse is $MPE=0.020$ $J/cm^2$. Thus, the exposure with the YAG laser at distance D=3 mm exceeds the MPE at by $ED/MPE=1.39/0.02 \approx 70$ times.

On the other hand, an ultrashort pulse laser uses a lower pulse energy to treat floaters. The threshold of the laser breakdown energy is proportional to the square root of the pulse duration. For example, a 300-femtosecond laser has $10000 \times 0.5=100$ times lower energy threshold than a 3-nanosecond laser. Thus, femtosecond lasers can treat a floater with a pulse energy of 10 to 30 microjoules (µJ), such as 15 to 20 µJ, which is about 100 times less than that of a YAG laser. The lower pulse energy yields lower retinal exposure that can satisfy the ANSI Retinal Maximum Permissible Exposure (MPE), which is $MPE=0.008$ $J/cm^2$ for a femtosecond pulse. Given pulse energy PE=20 µJ and laser beam numerical aperture NA=0.1, the floater-to-retina distance D that satisfies the MPE is $D>(20$ $µJ/(0.008$ $J/cm^2*0.2^2))^{0.5}=2.5$ mm. That is, the 20 µJ femtosecond pulse satisfies the MPE up to 2.5 mm away from the retina, while at 3 mm from the retina the 5 mJ nanosecond YAG pulse exceeds the MPE at by 70 times. In addition to providing for treatment that satisfies the MPE, the lower pulse energy also allows for multi-pulse treatment, which more effectively fragments a floater, and the lower pulse energy is less likely to cause a floater to jump unpredictably.

In certain embodiments, laser device 22 or the optical delivery system includes adaptive optics. The adaptive optics correct phase front errors of the laser beam to minimize the spot size of the laser beam, which in turn minimizes the required pulse energy (e.g., a few microjoules (µJ) to the nanojoule (nJ) range) and radiation exposure at the retina. In certain embodiments, adaptive optics are used to optimize the laser beam prior to treatment. In the embodiments, the laser beam is directed near the floater using subthreshold energy levels. A feedback signal (e.g., a two-photon fluorescence or a second harmonic feedback signal) from the vitreous is detected. Adaptive optics (e.g., an adaptive mirror) in the laser beam path are used to maximize the intensity of the feedback signal to minimize aberrations of the eye and the optical system.

In certain embodiments, laser device 22 includes an optical element that forms a Bessel or Bessel-like long focal length beam, which may increase the efficiency of floater destruction. In general, as compared with Gaussian beams, Bessel beams have a 1.6× smaller spot size, longer focal length (resulting in shorter treatment time), and larger divergence (yielding a larger spot size on the retina, reducing risk of retinal damage). Examples of optical elements that form Bessel or Bessel-like long focal length beams include an axicon, circular grating, proper phase plate, spatial light modulator (SLM), and Fabry-Perot interferometer.

Z-focusing component 32 longitudinally directs the focal point of the laser beam to a specific location in the direction of the floater shadow. In certain embodiments, z-focusing component 32 receives the z-location of the floater from interferometer device 21 (and may receive it via computer 26), and directs the laser beam towards the z-location of the floater. Z-focusing component 32 may include a lens of variable refractive power, a mechanically tunable lens, an electrically tunable lens (e.g., Optotune lens), an electrically or mechanically tunable telescope. In certain embodiments, laser device 22 or the optical delivery system also includes a fast xy-scanner used in tandem with z-focusing component 32 to, e.g., create a 3D focal spot pattern. Examples of such scanners include galvo, MEMS, resonant, or acousto-optical scanners.

Shared components 24 direct beams from SLO device 20, interferometer device 21, and laser device 22 towards the eye. Because SLO, interferometer, and/or laser beams share components 24, the beams are affected by the same optical distortions (e.g., fan distortion of scanners, barrel or pillow distortions of the scanner lens, refractive distortions from the inner eye surfaces, and other distortions). The distortions affect the beams in the same way, so the beams propagate along the same path. This allows for aiming the laser beam precisely at the floater.

As an overview of operation of shared components 24, mirror 42 directs a beam (SLO, interferometer, and/or laser beam) towards xy-scanner 40, which transversely directs the beam towards lens 44. Lenses 44 and 46 direct the beam towards eye. Shared components 24 may also provide spectral and polarization coupling and decoupling of SLO, interferometer, and laser beams to allow the beams to share the same path.

Turning to the details of shared components 24, in certain embodiments, xy-scanner 40 receives the xy-location of the floater shadow from SLO device 20, and directs the SLO, interferometer, and/or laser beam towards the xy-location. Xy-scanner 40 may be any suitable xy-scanner that transversely directs the focal point of the beam in the x- and y-directions and changes the angle of incidence of the beam into the pupil. For example, xy-scanner 40 includes a pair of galvanometrically-actuated scanner mirrors that can be tilted about mutually perpendicular axes. As another example, xy-scanner 40 includes an acousto-optical crystal that can acousto-optically steer the beam. As another example, xy-scanner 40 includes a fast scanner (e.g., a galvo, resonant, or acousto optical scanner) that can create, e.g., a 2D matrix of laser spots.

Xy-encoder 41 detects the angular position of xy-scanner 40 and reports the position as the xy-location measured in angular units. For example, xy-encoder 41 detects the angular orientations of the galvanometer mirrors of xy-scanner 40 in encoder units. Xy-encoder 41 may report the position in encoder units to SLO device 20, interferometer device 21, laser device 22, and/or computer 26. Since SLO device 20, interferometer device 21, and laser device 22 share xy-scanner 40, computer 26 can use the encoder units to instruct system 20 and device 22 where to aim their beams, making it unnecessary to perform the computer-intensive conversion from encoder units to a length unit such as millimeters.

Xy-encoder 41 reports the positions at any suitable rate, e.g., once every 5 to 50 milliseconds (ms), such as every 10 to 30 or approximately every 20 ms.

Shared components 24 also include optical elements. In general, an optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical elements include mirror 42 and lenses 44 and 46. Mirror 42 may be a trichroic mirror. Lenses 44 and 46 may be scanning optics of an SLO device.

Computer 26 controls components of system 10 in accordance with computer program 54. Examples of computer programs 54 include floater shadow imaging, floater shadow tracking, image processing, floater evaluation, retinal exposure calculation, patient education, and insurance authorization programs. For example, computer 26 controls components (e.g., floater detection system 19, laser device 24, and shared components 24) to image a floater and focus a laser beam at the floater. Computer program 54 may include instructions to create a pattern of laser pulses according to a scan pattern. Computer 26 may be separated from components or may be distributed among system 10 in any suitable manner, e.g., within floater detection system 19, laser device 24, and/or shared components 24. In certain embodiments, portions of computer 26 that control floater detection system 19, laser device 24, and/or shared components 24 may be part of floater detection system 19, laser device 24, and/or shared components 24, respectively.

In certain embodiments, computer 26 uses an image processing program 54 to analyze the digital information of the image to extract information from the image. In certain embodiments, image processing program 54 analyzes an image of a floater shadow to obtain information about the floater. For example, program 54 detects a floater by detecting a darker shape in an image (using, e.g., edge detection or pixel analysis) that may be the floater shadow. As another example, program 54 detects the shape and size of a floater shadow, which indicate the size and shape of the floater. As another example, program 54 detects the tone or luminance of the floater shadow, which indicates the density of the floater. In certain embodiments, computer 26 uses a tracking program 54 to track a floater shadow.

In certain embodiments, computer 26 determines the radiant exposure at the retina from a laser pulse directed at a particular z-location. The determination may consider any suitable factors, e.g., laser pulse energy, laser radiation wavelength, number of laser pulses, laser pulse duration, cone angle of the focused laser beam, and the focus to the retina. For example, the exposure can be calculated using the laser spot size of the laser beam and the distance between floater and retina. The radiant exposure should be less than a maximum radiant exposure, which may be determined in accordance with accepted standards. For example, the maximum radiant exposure may be set in accordance with ANSI Z80.36-2016. If the radiant exposure exceeds the maximum radiant exposure of the retina, lens, and/or IOL, computer 26 may modify any suitable factor (e.g., lower the pulse energy), provide a notification to the user, and/or prevent firing of the laser beam as an important safety feature.

In certain embodiments, computer 26 calculates safety factors that indicate radiation exposure relative to a maximum exposure standard. For example, a safety factor SF may take the form of: $SF=E/ME$, where E represents the exposure at the ocular tissue (e.g., retina or lens), and ME represents the maximum exposure, which may be defined by a standard. In certain situations, a standard allows the maximum exposure to be exceeded. For example, ANSI Z80.36-2016 does not apply to radiation for treatment of ocular tissues, and the stated MPE limit is about 10 times less than the experimentally determined retinal damage threshold. A surgeon can exceed the ANSI limits if the therapeutic advantage justifies the risk of the retinal exposure. The safety factors guide the surgeon in deciding whether or not the advantage justifies the risk.

Computer 26 calculates safety factors from values stored at computer 26, e.g., pulse energy, pulse duration, number of pulses in a pulse train, laser beam numerical aperture, laser beam wavelength, repetition rate, location of the laser focus (e.g., relative to the retina, lens, and/or IOL), and other parameters. Computer 26 may output the safety factors to the surgeon during surgery. If safety factor exceeds a predetermined amount (e.g., 10), computer 26 may notify the surgeon and/or prevent the surgery.

Examples of safety factors include:

(1) Retinal Safety Factor for Single Pulse $RSFSP=RE/MPESP$, where RE represents retinal exposure, and MPE represents a maximum exposure limit for a single pulse, e.g., the limit set by ANSI Z80.36-2016.

(2) Safety Factor for Average Retinal Exposure $SFARE=RE/ARE$ where RE represents retinal exposure, and ARE represents a maximum average power at the retina per unit area. The maximum average power may be, e.g., the limit set by ANSI Z80.36-2016 or a value determined from data. For example, given data from a million Femtosecond Laser Assisted Cataract Surgery (FLACS) surgeries, 11.0 W/cm$^2$ power density is considered safe.

(3) Safety Factor for Lens $SFL=LE/LMPE$, where LE represents the lens exposure and LVPE represents a maximum exposure. ANSI does not set safety limits for lenses (natural and IOL), but since lenses are less sensitive to the laser radiation than the retina, values safe for the retina should also be safe for the lens.

Involuntary and voluntary eye movements (e.g., saccadic and micro-saccadic movements, drift, and tremor) can make laser treatment difficult. To reduce movement, the eye can be stabilized during treatment in any suitable manner to reduce movement of the eye. For example, the treated eye and/or the other eye can be stabilized using a fixation light. As another example, a patient interface or handheld surgical contact lens can be used to mechanically stabilize the eye. In addition, movement of the treated eye and/or the other eye can be tracked in any suitable manner. Any suitable portion of the eye (e.g., pupil, pupil edge, iris, blood vessels) and/or reflections from the eye (e.g., Purkinje reflections) can be tracked.

Figure 2:
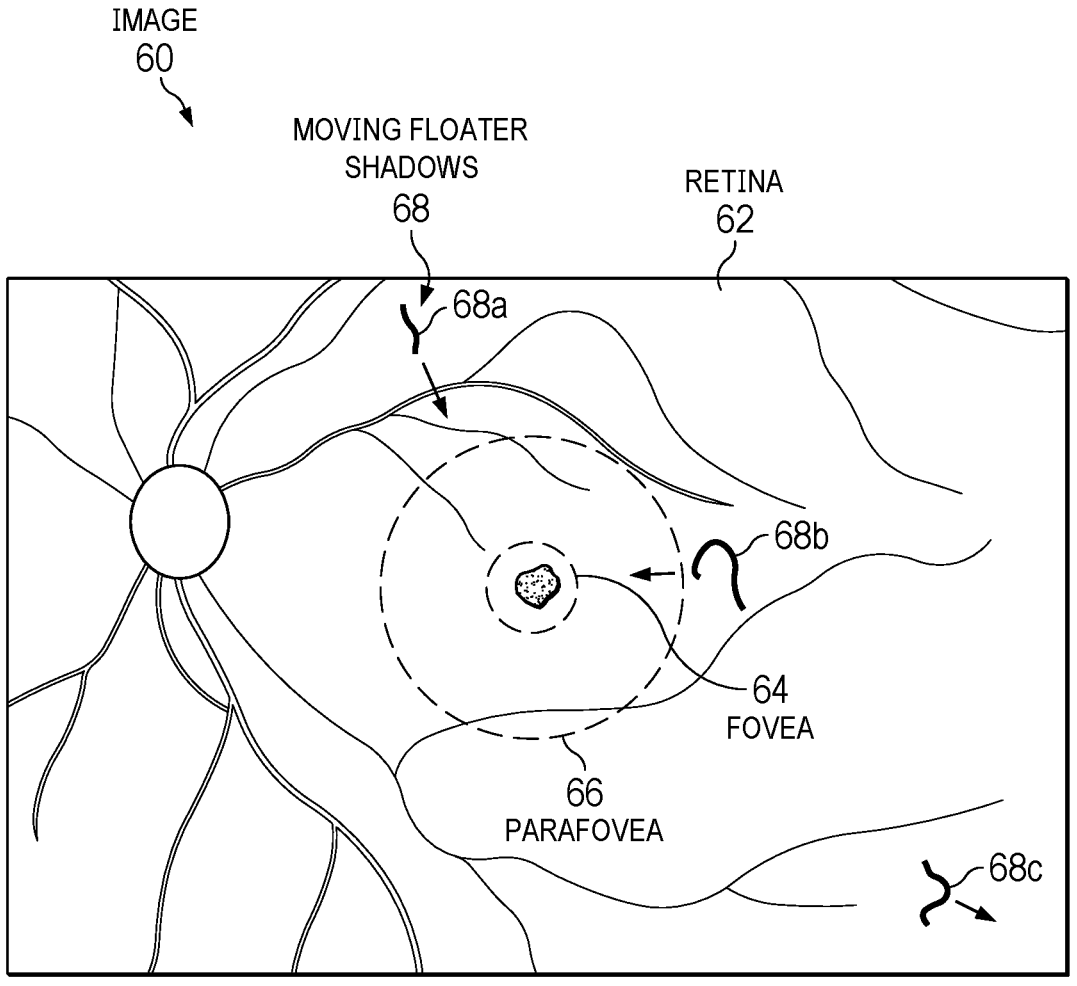
FIG. 2 illustrates an example of a retinal image that may be generated by the system of FIG. 1.

FIG. 2 illustrates an example of a retinal image 60 that may be generated by system 10 of FIG. 1. Image 60 shows the retina 62 of an eye, with a foveal region (or fovea) 64 and a parafoveal region (or parafovea) 66. Generally, fovea 64 has a visual angle of approximately +/−one degree, and parafovea 66 has a visual angle of approximately +/−seven degrees. Image 60 also shows floater shadows 68 (68a, 68b, 68c) that floaters cast on retina 62. In general, non-moving shadows are not caused by floaters, and may be caused by, e.g., corneal or lens opacities or anatomical changes of the retina, so floater treatment is not concerned with non-moving shadows.

A floater may be regarded as clinically significant if it can cause a visual disturbance, which can be determined from any suitable features of the floater shadow, e.g., the size and/or density of the shadow, proximity of the shadow to the fovea and/or parafovea, and/or the track of the shadow relative to the fovea and/or parafovea. As an example, a floater can cause a visual disturbance if it permanently or transiently casts a shadow 68 on fovea 64 or can cause distraction or annoyance if it permanently or transiently casts a shadow 68 on parafovea 66. Accordingly, if a floater shadow falls within or is predicted to move within fovea 64 and/or parafovea 66, the floater may be designated as clinically significant. As another example, floater shadow 68 can be used to estimate the size and density of the floater. Larger, denser floaters are more likely to cause a visual disturbance. Thus, a shadow 68 larger than a critical shadow size can indicate a clinically significant floater. A shadow 68 with a higher contrast relative to the background may indicate a clinically significant floater.

Figure 3:
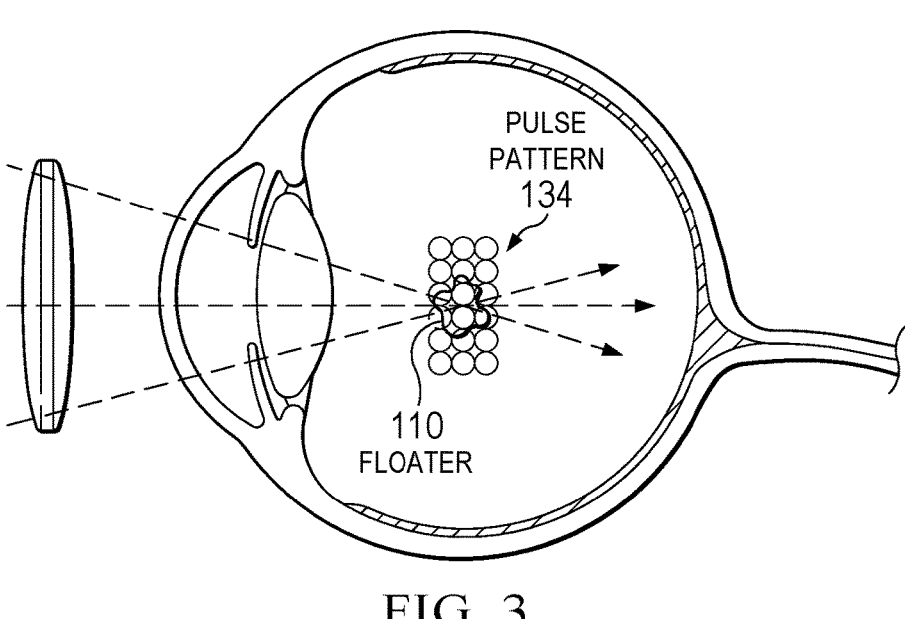
FIGS. 3, 4A, and 4B illustrate an example of a three-dimensional (3D) pulse pattern that may be created by the system of FIG. 1, according to certain embodiments.
Figure 4A:
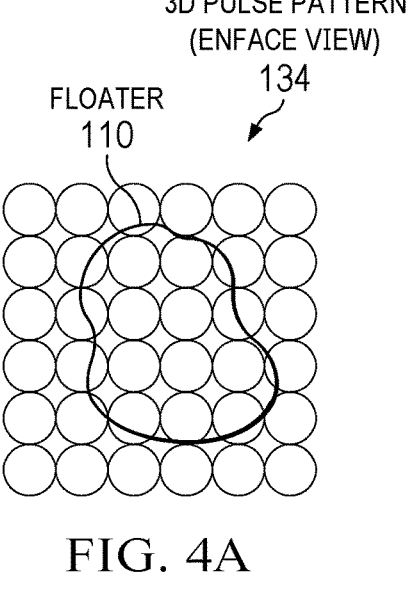
Figure 4B:
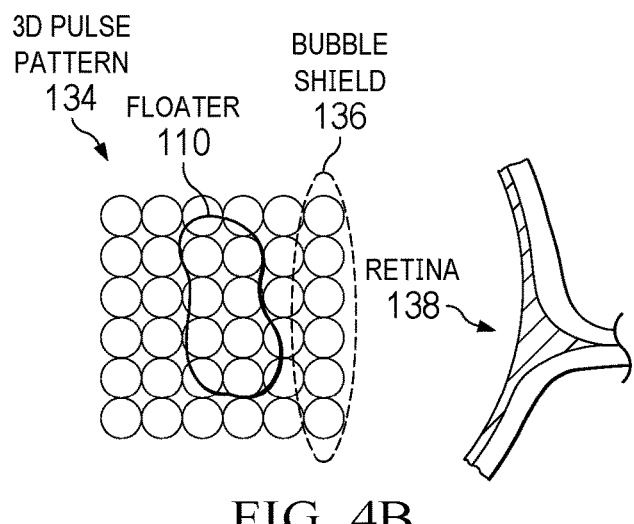

FIGS. 3, 4A, and 4B illustrate an example of a three-dimensional (3D) pulse pattern 134 that may be created by system 10 of FIG. 1, according to certain embodiments. FIG. 3 shows pulse pattern 134 within the eye. FIG. 4A shows pulse pattern 134 in the enface view, and FIG. 4B shows pulse pattern 134 relative to retina 138. In certain embodiments, three-dimensional (3D) pulse pattern that may more effectively fragment floater 110 and may include a bubble shield that reduces retinal radiation exposure at the retina of the eye.

The laser pulses of 3D pulse pattern 134 create rapidly expanding cavitation bubbles that disintegrate floater 110. For example, a 20 microjoules femtosecond laser pulse creates a cavitation bubble with a maximum transient diameter of approximately 400 micrometers ($\mu$m), which expands and collapses within approximately 38 milliseconds (ms). The acceleration of the bubble wall-tissue interface is approximately 107 meter/second$^2$ (m/s$^2$), i.e., approximately 1,000,000 G, which functions like a violent explosion that disintegrates the collagen fibers of a floater. The cavitation bubbles expand and contract several times, growing smaller with each iteration. After a few iterations, the water vapors within the bubbles condense into water and some gases (e.g., hydrogen, oxygen, CO2, and NOX) remain inside of the bubbles. After 30 seconds to a few minutes, the bubbles dissolve in the vitreous and upward forces lift the bubbles away from the visual field. While alive, posterior bubbles form a bubble shield, an opaque layer that shields the retina from exposure by subsequent anterior pulses.

3D pulse pattern 134 may have any suitable size and shape. In certain embodiments, pattern 134 may be a rectangular cuboid (e.g., a cube) of pulses. The sides may have any suitable dimensions (e.g., 10 to 2000 $\mu$m, such as 100 to 1500 $\mu$m) with any suitable pulse separation (e.g., 10 to 1000 $\mu$m, such as 100 to 500 $\mu$m). The posterior layer (e.g., enface layer) of pulses operates as a bubble shield 136 that protects the retina 138. Pattern 134 may be formed in any suitable manner, e.g., starting from posterior layers to anterior layers. In some embodiments, posterior layers, e.g., the bubble shield, are formed with a lower repetition rate (e.g., 1000 to 2000 hertz (Hz), such as 1080 Hz) and/or lower pulse energy (e.g., 10 to 15 $\mu$J) to protect the retina, and anterior layers are then formed with a higher rep rate (e.g., 2000 to 100,000 Hz, such as 15,000 to 50,000 Hz) and/or higher pulse energy (e.g., 15 to 35 $\mu$J, such as 20 to 30 $\mu$J).

Examples of pulse patterns 134 include:
(1) Pulse pattern 134 is a 3×3×3 matrix of pulses separated by 400 micrometers ($\mu$m). The first plane of nine pulses form the bubble shield at the posterior part of the floater at a lower repetition rate (e.g., 1080 hertz (Hz)). The bubble shield shields the retina from the remaining 18 pulses, so they can be delivered at higher repetition rate (e.g., 5000 Hz). The total treatment time is approximately 12 milliseconds (ms).
(2) Pulse pattern 134 is a 10×10×10 matrix of pulses separated by 100 $\mu$m. The pattern may treat a 1 mm floater. The first plane 100 laser pulses form the bubble shield posterior to the floater by about 300 $\mu$m at a lower repetition rate (e.g., 541 Hz) and lower pulse energy (e.g., 10 microjoules ($\mu$J)). The bubble shield shields the retina from the remaining 900 pulses, so they can be delivered at higher repetition rate (e.g., 5000 Hz) and/or pulse energy (e.g., 20 $\mu$J). The total treatment time is approximately 0.365 seconds.
(3) Pulse pattern 134 is a 15×15×8 matrix of 1800 pulses separated by 100 $\mu$m in the x- and y-directions and 200 $\mu$m in the z-direction. The pattern may treat a 1.5 mm floater. The repetition rate is 50,000 Hz, and the laser pulse energy 10 $\mu$J. The treatment time is approximately 0.036 seconds.
(4) Pulse pattern 134 is a 15×15×15=3375 3D matrix of pulses separated by 100 um. The pattern may treat a 1.5 mm floater. At a repetition rate of 50,000 Hz, treatment time is 3375/50,000=0.0675 seconds.

In certain embodiments, the 3D pulse pattern 134 provides safe average laser power per area (APD) of the retina. From data from millions of FLACS surgeries, the average laser power per area APD=11.0 W/cm$^2$ appears to be safe. A 3D pulse pattern 134 can satisfy this value. For example, given pulse energy 20 microjoules ($\mu$J), repetition rate 1080 Hertz (Hz), floater-to-retina distance 2.5 millimeters (mm), and full angle numerical aperture 0.2, APD=1080 Hz*20 $\mu$J/[(2.5 mm*0.2)$^2$*7$\pi$/4]=~11.0 W/cm$^2$. As another example, given pulse energy 30 $\mu$J, repetition rate 15,000 Hz, floater-to-retina distance 12 mm, and full angle numerical aperture 0.2, APD=15,000 Hz*30 $\mu$J/[(12 mm*0.2)$^2$*$\pi$/4]=~10 W/cm$^2$.

Figure 5:
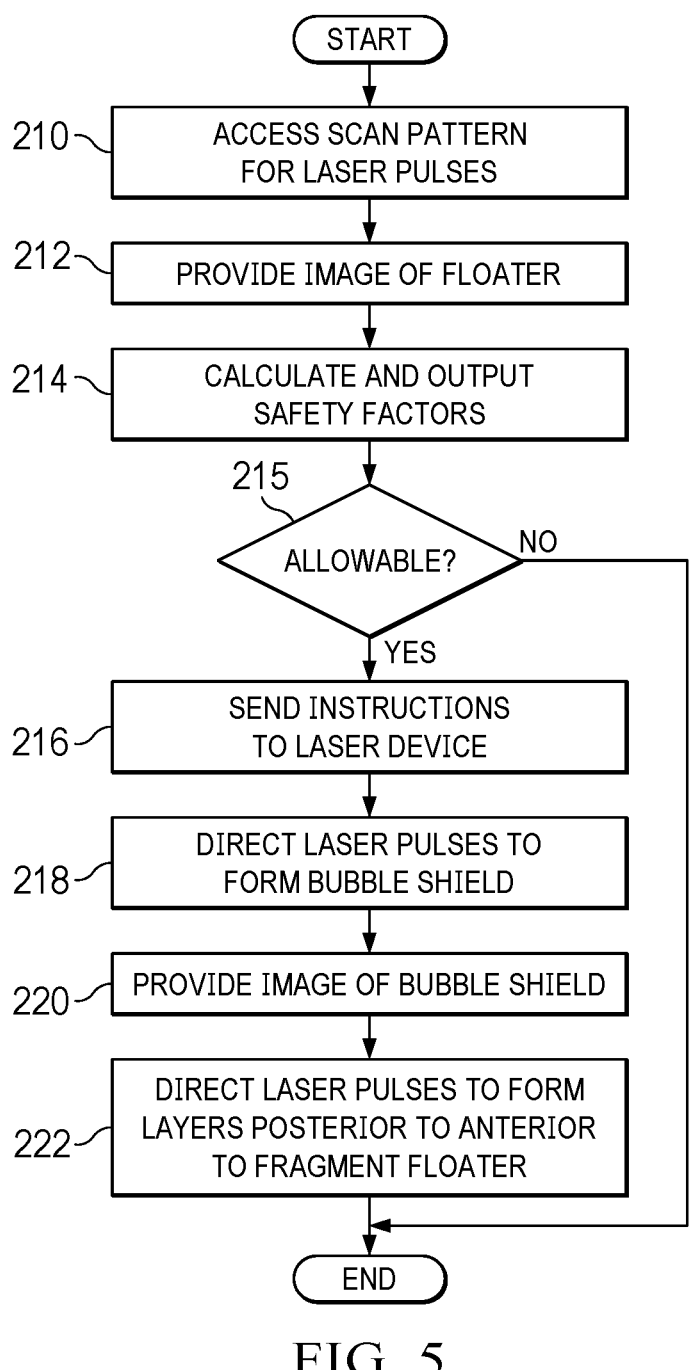
FIG. 5 illustrates an example of a method for fragmenting a floater with a three-dimensional (3D) scan pattern that may be performed by the system of FIG. 1, according to certain embodiments.

FIG. 5 illustrates an example of a method for fragmenting a floater with a three-dimensional (3D) scan pattern that may be performed by system 10 of FIG. 1, according to certain embodiments. A user such as a surgeon may use a 3D pulse pattern to fragment a floater within the vitreous of a patient eye. The 3D pulse pattern includes a bubble shield that reduces retinal radiation exposure at the retina of the eye.

The method starts at step 210, where computer 26 accesses the 3D scan pattern for laser pulses. The scan pattern may be stored in memory 52. Floater detection system 19 provides an image of the floater to the user at step 212. The image may allow the user to locate the floater. Computer 26 calculates and outputs safety factors at step 214. Safety factors indicate radiation exposure in the eye relative to a maximum exposure limit. They guide the user in deciding whether or not the advantage of the surgery justifies the risk of retinal radiation exposure. The treatment may be allowable at step 215. If the treatment is allowable, the method proceeds to step 216. If it is not, the method ends.

Computer 26 sends instructions to laser device 22 to direct pulses towards the eye according to the scan pattern at step 216. Any suitable 3D scan pattern, e.g., as described herein, may be used. Laser device 22 directs laser pulses towards the eye to form bubble shield within the vitreous at step 218. The bubble shield reduces retinal radiation exposure at the retina of the eye. Floater detection system 19 provides an image of the bubble shield to the user at step 220. The image may allow the user to check that the bubble shield is sufficiently opaque to protect the retina. Laser device 22 directs laser pulses to form layers, from posterior to anterior layers, to fragment floater at step 222.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

what is claimed:

1. An ophthalmic laser surgical system for treating a floater in an eye, comprising:

a floater detection system configured to determine a location of the floater in the eye;

a laser device configured to direct a laser beam along a laser beam path towards the floater; and a computer configured to:

calculate a radiant exposure at a component of the eye according to a floater-to-component distance between a z-location of the floater and the component;

calculate a safety factor from the radiant exposure, the safety factor describing a mathematical relationship between the radiant exposure and a maximum exposure;

determine if directing the laser beam along the laser beam path towards the floater is allowable according to a predetermined boundary of the safety factor;

instruct the laser device to direct the laser beam along the laser beam path towards the floater if that is allowable; and if directing the laser beam along the laser beam path towards the floater is not allowable, prevent the laser device from directing the laser beam towards the floater.

2. The ophthalmic laser system of claim 1, the safety factor equal to the ratio of the maximum exposure and the radiant exposure.

3. The ophthalmic laser system of claim 1, wherein:

the radiant exposure describes radiant exposure at a retina of the eye; and the maximum radiant exposure describes a maximum radiant exposure for a single pulse at the retina.

4. The ophthalmic laser system of claim 1, wherein:

the radiant exposure describes radiant exposure at a retina of the eye; and the maximum radiant exposure describes a maximum average power at the retina.

5. The ophthalmic laser system of claim 1, wherein:

the radiant exposure describes radiant exposure at a lens of the eye; and the maximum exposure describes a maximum radiant exposure at the lens.

6. The ophthalmic laser system of claim 1, the computer configured to calculate the radiant exposure at the component of the eye according to the z-location of the floater by:

determining a laser spot size of the laser beam on the component; and calculating the radiant exposure according to the laser spot size of the laser beam and the floater-to-component distance.

7. The ophthalmic laser system of claim 1, the computer configured to:

calculate a closest floater-to-component distance at which the eye can be treated, given a laser pulse energy of the laser beam.

8. The ophthalmic laser system of claim 1, the computer configured to:

calculate a maximum laser pulse energy at which the eye can be treated, given the floater to-component distance.

9. The ophthalmic laser system of claim 1, wherein the floater detection system is configured to determine the location of the floater based on a location of a shadow of the floater cast at a retina of the eye.

* * * * *